United States Patent [19]

Briscoe et al.

[11] 4,242,906
[45] Jan. 6, 1981

[54] THERMOCOUPLE-EQUIPPED, SOIL PROBE WITH REMOVABLE PROTECTIVE SHIELD

[75] Inventors: Ralph D. Briscoe, Providence; Wayne K. Barlow, Logan, both of Utah

[73] Assignee: Wescor, Inc., Logan, Utah

[21] Appl. No.: 72,152

[22] Filed: Sep. 4, 1979

[51] Int. Cl.³ .................... G01N 25/56; G01K 1/16
[52] U.S. Cl. ......................... 73/73; 73/336.5; 136/232
[58] Field of Search ................ 73/73, 86; 136/233, 136/232, 230

[56] References Cited

U.S. PATENT DOCUMENTS

| | | | |
|---|---|---|---|
| 2,430,887 | 11/1947 | Ray | 136/232 |
| 2,915,575 | 12/1959 | Thomas | 136/232 X |
| 3,293,907 | 12/1966 | Schnatz et al. | 73/73 |
| 3,430,486 | 3/1969 | Richards | 73/73 |
| 3,897,272 | 7/1975 | Medlar | 136/230 |
| 4,117,926 | 10/1978 | Turner et al. | 136/232 X |

FOREIGN PATENT DOCUMENTS 130694  12/1959  U.S.S.R. ....................... 73/73

Primary Examiner—Daniel M. Yasich
Attorney, Agent, or Firm—Mallinckrodt & Mallinckrodt

[57] ABSTRACT

An in-situ, thermocouple, soil hygrometer or psychrometer probe equipped with a removable, moisture pervious thermocouple shield, so that the thermocouple may be periodically cleaned for increased life and improved performance, has an elastic, protective boot that retains the shield in place about the thermocouple and permits easy removal of such shield. The boot is made of low-vapor sink material, so as not to interfere with proper operation of the thermocouple, and is configured to firmly grip the thermocouple mount, so that pulling of the thermocouple from its lead wires during removal and replacement of the shield is avoided.

6 Claims, 3 Drawing Figures

THERMOCOUPLE-EQUIPPED, SOIL PROBE WITH REMOVABLE PROTECTIVE SHIELD

BACKGROUND OF THE INVENTION

1. Field

The invention is in the field of thermocouple hygrometer or psychrometer probes adapted for in situ, soil-moisture-content measurements.

2. State of the Art

The problem of contamination of thermocouples in hygrometer or psychrometer probes used for water potential measurement has been recognized for many years. However, none of the available probes have permitted easy cleaning of the thermocouple after use. Typically, a heat shrunk, non-elastic, plastic boot has been used to permanently secure the usual thermocouple shield and protect the electrical lead connections to the thermocouple. Attempts have been made to friction fit the thermocouple shield upon the thermocouple block, but the shields have not been satisfactorily retained. Threading the shield and the thermocouple block together has proven too expensive. Attempts to provide elastic coupling of the shield and the thermocouple block have failed because the elastic material of the shield has not retained its elasticity after extended use, or has been a strong vapor sink, thereby adversely affecting thermocouple performance.

SUMMARY OF THE INVENTION

The probe device of the invention comprises a thermocouple carried by a mounting block therefor, and a rigid, moisture-pervious shield fitted over the mounting block as a cap protectively covering the thermocouple. A retaining boot for the thermocouple shield is of elongate, open-ended, tubular formation and of elasticity retentive, elastic material having low vapor-sink properties. It is configured to elastically engage such block, as well as to protectively encase the electrical lead connections to the thermocouple and to fit snugly about the electrical supply cable therefor.

THE DRAWING

An embodiment representing the best mode presently contemplated for carrying out the invention is illustrated in the accompanying drawing, wherein:

FIG. 1, is a pictorial view of the probe device ready for use;

FIG. 2, a longitudinal, axial section taken on the line 2—2 of FIG. 1 and showing the device in use; and FIG. 3, a transverse section taken on the line 3—3 of FIG. 1 and drawn to a somewhat larger scale.

DETAILED DESCRIPTION OF THE ILLUSTRATED EMBODIMENT

Figure 1:
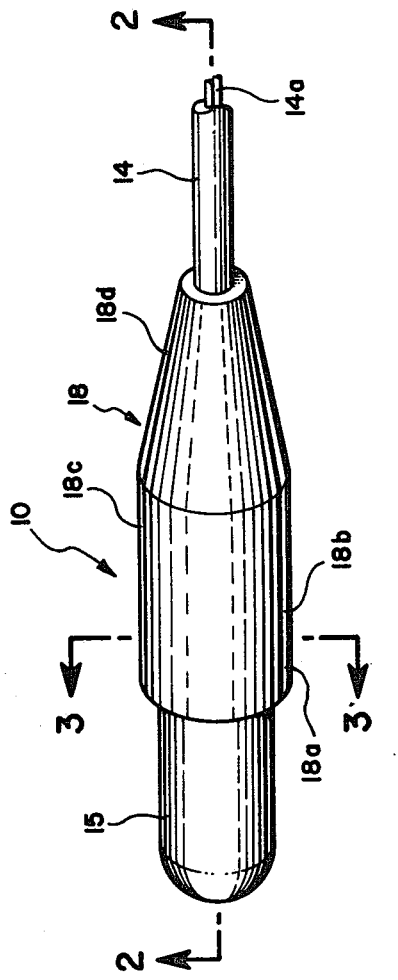
Figure 3:
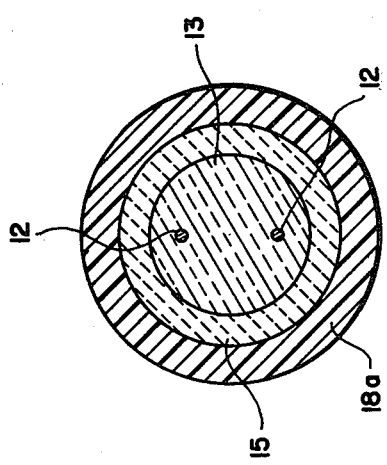
Figure 2:
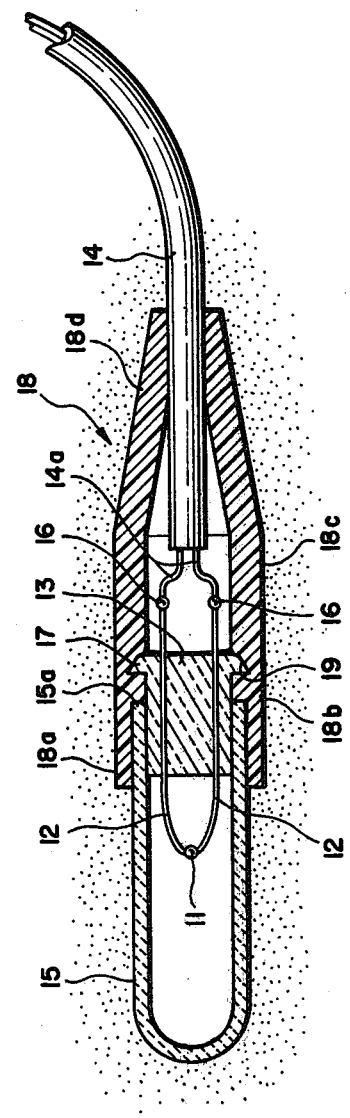

In the illustrated form of the invention, the probe device is indicated generally 10, being shown in FIG. 2 as installed in soil whose water potential is to be measured. It comprises a thermocouple junction 11, thermocouple wires 12, thermocouple mounting block 13, electrical lead wires 14, and a vapor-pervious, thermocouple shield 15. Connections 16 of any suitable type join thermocouple wires 12 to individual wires 14a of an electrical supply cable 14.

In operation of the device as so far described, it is well known that water vapor from the soil passes through the shield 15 and tends to change the temperature of the thermocouple junction 11. The moisture content, i.e. water potential or osmolality of the soil, is ultimately derived from this temperature change, as described by way of example in U.S. Pat. No. 3,797,312, entitled "Thermocouple Hygrometer and Method". A disadvantage is that junction 11 tends to become contaminated, thereby affecting the accuracy of measurements made and ultimately rendering the device inoperative. Periodic cleaning of junction 11 would both extend the operating life of the thermocouple and improve its accuracy.

In accordance with the invention, thermocouple mounting block 13 is provided with a boot-engaging formation, preferably an outwardly protruding, circumferential shoulder 17 and there is provided an elastic boot 18 of open-ended, elongate, tubular construction. Boot 18 is configured to provide an open end portion 18a of slightly less diameter than the diameter of shield 15 so as to tightly grip such shield, a next portion 18b having a formation, here a circumferential groove 19, adapted to engage and mate with the thermocouple mounting block formation 17, a next portion 18c adapted to protectively encase thermocouple lead wires 14 and their connections 16 with wires 14a of cable 14, and an open end portion 18d adapted to closely encircle electrical supply cable 14. Boot 18 is made of an elastic material which will retain its elasticity under the conditions of use of the device and which is not a strong vapor sink. Vinyl rubber has proven satisfactory in these respects.

The elasticity of the material of boot 18 provides for tight, waterproof gripping of the open end portion 15a of shield 15, which holds it firmly in place during use of the device. However, when it is desired to clean thermocouple juntion 11 and its environs, shield 15 can be easily pulled free of its frictional engagement with boot 18 to expose the thermocouple. Following the cleaning operation, shield 15 can be easily replaced by reinserting it into the open end portion 18a of the boot.

It is preferred that the thermocouple mounting block 13 be molded to shape from "Teflon" plastic or the like so as to encase portions of the thermocouple wires 12 as electrical insulation therefor and to provide structural rigidity for shoulder 17 of the mounting block effective to prevent pulling away of such block from boot 18 when shield 15 is pulled free of both the block and the boot. This insures that the integrity of electrical connections 16 will be maintained during removal of shield 15 as previously described.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims which follow.

We claim:

1. A probe for a soil hygrometer or psychrometer, comprising a thermocouple; a mounting block for the thermocouple; a vapor-permeable, thermocouple shield removably engaging said block and protectively encasing the thermocouple; and a tubular, shield-retaining, elastic boot tightly engaging the shield and interlocked with the block, so the shield may be easily removed by pulling it free of the block and the boot and may be subsequently replaced.

2. A probe in accordance with claim 1, including an electrical supply cable electrically connected to the thermocouple, and wherein the boot is sufficiently elongate to encase the electrical connections and to elastically engage the cable.

3. A probe in accordance with claim 1, wherein the block and the boot are provided with mated, interengaging formations as the interlock therebetween to prevent pulling of the block when the shield is pulled.

4. A probe in accordance with claim 3, wherein the mated formations comprise an external circumferential projection on the block, and an internal circumferential groove in the boot.

5. A probe in accordance with claim 1, wherein the boot is of elasticity-retaining elastic material having low vapor-sink properties.

6. A probe in accordance with claim 5, wherein the boot is of vinyl rubber.

* * * * *